(12) United States Patent
Wei et al.

(10) Patent No.: US 11,593,468 B2
(45) Date of Patent: Feb. 28, 2023

(54) SYSTEM AND METHOD FOR IDENTIFYING USER

(71) Applicant: VITA-COURSE TECHNOLOGIES CO., LTD., Shenzhen (CN)

(72) Inventors: Chuanmin Wei, Shenzhen (CN); Heng Peng, Shenzhen (CN); Jiwei Zhao, Shenzhen (CN)

(73) Assignee: Vita-Course Technologies Co., Ltd., Shenzhen (CN)

( * ) Notice: Subject to any disclaimer, the term of this patent is extended or adjusted under 35 U.S.C. 154(b) by 377 days.

(21) Appl. No.: 16/804,640

(22) Filed: Feb. 28, 2020

(65) Prior Publication Data

US 2020/0201971 A1 Jun. 25, 2020

Related U.S. Application Data

(63) Continuation of application No. PCT/CN2017/099780, filed on Aug. 30, 2017.

(51) Int. Cl.
*G06F 21/32* (2013.01)
*G06N 20/10* (2019.01)
(Continued)

(52) U.S. Cl.
CPC ............ *G06F 21/32* (2013.01); *A61B 5/0006* (2013.01); *G06N 3/08* (2013.01); *G06N 20/10* (2019.01); *G06V 40/70* (2022.01); *G06V 40/15* (2022.01)

(58) Field of Classification Search
CPC . G06F 21/32; G06F 3/01; G06F 21/36; G06F 3/011; G06F 2203/011;
(Continued)

(56) References Cited

U.S. PATENT DOCUMENTS

| | | | |
|---|---|---|---|
| 2015/0125832 A1* | 5/2015 | Tran | G09B 5/00 434/127 |
| 2016/0063233 A1* | 3/2016 | Bae | G07C 9/37 726/19 |

(Continued)

FOREIGN PATENT DOCUMENTS

| | | |
|---|---|---|
| CN | 101773394 A | 7/2010 |
| CN | 106650685 A | 5/2017 |
| EP | 2989967 A1 | 3/2016 |

OTHER PUBLICATIONS

International Search Report in PCT/CN2017/099780 dated May 30, 2018, 5 pages.

(Continued)

*Primary Examiner* — Nimesh Patel
(74) *Attorney, Agent, or Firm* — Bay State IP, LLC

(57) ABSTRACT

A method may include acquiring first physiological data relating to a first subject, extracting at least one first physiological feature from the first physiological data relating to the first subject, determining a first model relating to at least one first reference physiological feature, generating, based on the first model and the at least one first physiological feature, a second model, the second model relating to at least one second reference physiological feature corresponding to the second model, and determining, based on the second model and the at least one first physiological feature, at least one identification physiological feature relating to the first subject. In some embodiments, the at least one identification physiological feature may correspond to the at least one second reference physiological feature.

9 Claims, 9 Drawing Sheets

(51) Int. Cl.
*A61B 5/00* (2006.01)
*G06N 3/08* (2023.01)
*G06V 40/70* (2022.01)
*G06V 40/10* (2022.01)

(58) Field of Classification Search
CPC ........ G06F 40/30; G06F 3/012; G06F 16/436; G06F 3/015; G06F 3/0482; G06F 3/048; G06F 16/54; G06F 3/0481; A61B 5/0006; G06N 3/08; G06N 20/10; G06N 3/0454; G06N 20/00; G06N 3/04; G06N 3/004; G06N 3/008; G06N 5/022; G06N 5/003; G06V 40/70; G06V 40/15; G06V 40/172; G06V 20/52; G06V 40/168; G06V 40/50; G06V 20/41; G06V 40/167; G06V 40/169; G06V 40/174; G06V 40/1365; G06V 10/17; G06V 40/193; G06V 40/103; G06V 40/165; G06V 40/176; G06V 40/20; G06V 40/10; G06V 40/16; G06V 40/161; G06K 9/6215; G06K 9/6272; G06K 9/6256; G06K 9/6267; G06K 9/00; G06K 9/6268; G06K 9/6201; G06K 9/6218; G06K 9/6292; G08B 21/182; G08B 3/10; H04M 1/72454; H04M 2250/52; H04M 1/72463; H04N 5/23219; H04N 5/23238; G06Q 30/0631; G06Q 50/01; G06Q 30/0643; G06Q 30/0282; G06Q 30/06; G06Q 30/0277; G06Q 30/0281; G06Q 30/0627; G06Q 30/0253; G06Q 30/0254; G06Q 30/0267; G06Q 30/0637

See application file for complete search history.

(56) References Cited

U.S. PATENT DOCUMENTS

| | | |
|---|---|---|
| 2016/0191517 A1 | 6/2016 | Bae et al. |
| 2017/0091595 A1 | 3/2017 | Wang et al. |
| 2018/0310841 A1* | 11/2018 | Khwaja ................ A61B 5/1116 |
| 2018/0330116 A1* | 11/2018 | He .......................... G06F 21/31 |

OTHER PUBLICATIONS

Written Opinion in PCT/CN2017/099780 dated May 30, 2018, 4 pages.

* cited by examiner

420

Registration Unit 520

First Feature Extraction Sub-Unit 522

Model Generation Sub-Unit 524

Identification Information Determination Sub-Unit 526

Identification Unit 540

Second Feature Extraction Sub-Unit 542

Judgment Sub-Unit 544

Calculation Sub-Unit 546

Storage Unit 560

FIG. 5

SYSTEM AND METHOD FOR IDENTIFYING USER

CROSS-REFERENCE TO RELATED APPLICATIONS

This application is a continuation of International Application No. PCT/CN2017/099780, filed on Aug. 30, 2017, which designates the United States of America, the contents of which are incorporated herein by reference in their entirety.

TECHNICAL FIELD

The present disclosure generally relates to user identification systems, and more specifically relates to methods and systems for identifying a user based on physiological signals.

BACKGROUND

The biometric technology for personal identification by utilizing signals, such as voice signals and personal data extracted from a body, has been used in various fields, such as those of security and fraud detection. Exemplary biometric technologies may include fingerprint identification, voice identification, vein identification, iris recognition, retina recognition, facial recognition, DNA recognition, or the like, or a combination thereof. However, the bio-signal mentioned above (e.g., fingerprint, vein, voice, etc.) may be stolen, lost, or forged, which may compromise the accuracy of identification. It is thus desirable to provide systems and methods for identifying a user effectively based on physiological signals.

SUMMARY

According to an aspect of the present disclosure, a method for identifying a user based on physiological signals is provided. The method may be implemented on at least one machine each of which has at least one processor and storage. The method may include acquiring first physiological data relating to a first subject, extracting at least one first physiological feature from the first physiological data relating to the first subject, determining a first model relating to at least one first reference physiological feature, generating, based on the first model and the at least one first physiological feature, a second model, the second model relating to at least one second reference physiological feature corresponding to the second model, and determining, based on the second model and the at least one first physiological feature, at least one identification physiological feature relating to the first subject In some embodiments, the at least one identification physiological feature may correspond to the at least one second reference physiological feature.

In some embodiments, the first physiological data relating to the first subject may include at least one of an electrocardiogram (ECG) signal or a photoplethysmogram (PPG) signal.

In some embodiments, the determining a first model relating to at least one first reference physiological feature may further include acquiring multiple physiological data relating to multiple subjects, extracting physiological features relating to the multiple subjects from the multiple physiological data, and training a machine learning model based on the physiological features relating to the multiple subjects to generate the first model.

In some embodiments, the machine learning model may be constructed based on at least one of a conventional neural network, a long short-term memory network, a deep belief network, a generative adversarial network, a support vector machine, or a random forest model.

In some embodiments, the determining, based on the first model and the at least one first physiological feature, a second model may further include determining at least one effective physiological feature based on the first model and the at least one first physiological feature, the at least one effective physiological feature corresponding to the at least one first reference physiological feature and training the first model by the at least one effective physiological feature to generate the second model corresponding to the first subject.

In some embodiments, the determining, based on the first model and the at least one first physiological feature, a second model may further include acquiring second physiological data relating to the first subject, the second physiological data corresponding to the first physiological data, generating a third model based on the first model and the at least one first physiological feature, the second model relating to at least one third reference physiological feature corresponding to the third model, and generating the second model by training the third model based on the second physiological data.

In some embodiments, the second physiological data relating to the first subject may include at least one of blood pressure data, blood glucose data, heart rate data, or respiration rate data and the at least one first physiological feature includes at least one of an electrocardiogram (ECG) signal or a photoplethysmogram (PPG) signal.

In some embodiments, the method may further include identifying a second subject based on the at least one identification physiological feature relating to the first subject.

In some embodiments, the identifying a second subject based on the second model and the at least one first physiological feature relating to the first subject, may further include acquiring the at least one identification physiological feature relating to the first subject, determining at least one second physiological feature relating to the second subject, comparing the at least one second physiological feature relating to the second subject and the at least one identification physiological feature relating to the first subject, and identifying the second subject based on the comparison.

In some embodiments, the determining at least one second physiological feature relating to the second subject, may further include acquiring at least one of the first model or the second model and determining the at least one second physiological feature relating to the second subject based on the at least one of the first model or the second model.

In some embodiments, the comparing the at least one second physiological feature relating to the second subject and the at least one identification physiological feature relating to the first subject, may further include determining a feature vector based on the at least one identification physiological feature relating to the first subject, determining a second feature vector based on the at least one second physiological feature relating to the second subject, determining a distance between the feature vector relating to the first subject and the second feature vector relating to the second subject, and comparing the distance between the first feature vector relating to the first subject and the second feature vector relating to the second subject with a threshold.

In some embodiments, the method may further include determining, in response to the determination that the distance is lower than or equal to the threshold, that the second subject matches with the first subject.

According to an aspect of the present disclosure, a system for identifying a user based on physiological signals is provided. The system may include at least one processor and executable instructions. When the executable instructions are executed by the at least one processor, the instructions may cause the system to implement a method. The method may include acquiring first physiological data relating to a first subject, extracting at least one first physiological feature from the first physiological data relating to the first subject, determining a first model relating to at least one first reference physiological feature, generating, based on the first model and the at least one first physiological feature, a second model, the second model relating to at least one second reference physiological feature corresponding to the second model, and determining, based on the second model and the at least one first physiological feature, at least one identification physiological feature relating to the first subject. The at least one identification physiological feature may correspond to the at least one second reference physiological feature.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include acquiring first physiological data relating to a first subject, extracting at least one first physiological feature from the first physiological data relating to the first subject, determining a first model relating to at least one first reference physiological feature, generating, based on the first model and the at least one first physiological feature, a second model, the second model relating to at least one second reference physiological feature corresponding to the second model, and determining, based on the second model and the at least one first physiological feature, at least one identification physiological feature relating to the first subject. The at least one identification physiological feature may correspond to the at least one second reference physiological feature.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a block diagram illustrating an exemplary processing module according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
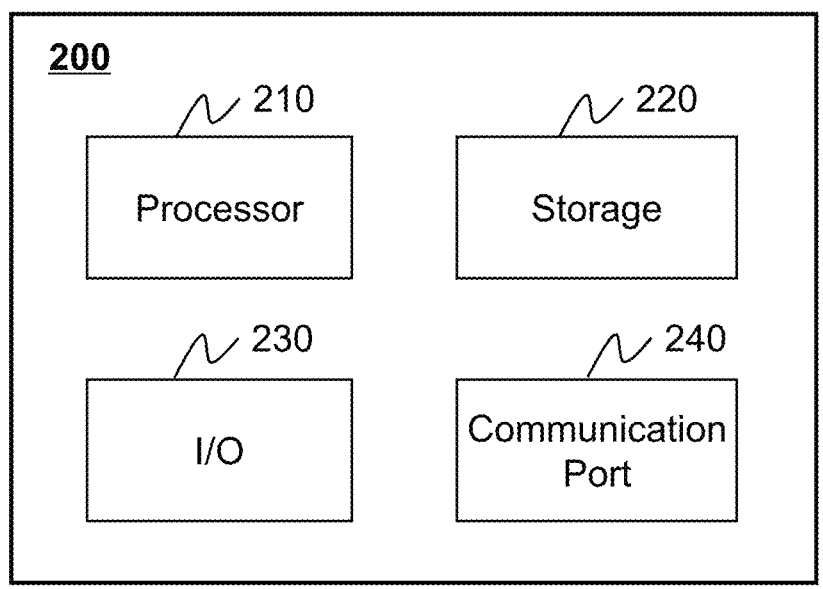
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for user identification. In some embodiments, a physiological signal (e.g., a PPG, an ECG, etc.) may be used to identify a user. For example, one or more identification physiological features may be determined based on the physiological signal used to identify the subject. The method for determining an identification physiological feature may include acquiring first physiological data relating to a first subject; extracting at least one first physiological feature from the first physiological data relating to the first subject; determining a first model relating to at least one first reference physiological feature; generating, based on the first model and the at least one first physiological feature, a second model, the second model relating to at least one second reference physiological feature corresponding to the second model; and determining, based on the second model and the at least one first physiological feature, at least one identification physiological feature relating to the first subject wherein the at least one identification physiological feature corresponds to the at least one second reference physiological feature. In some embodiments, the method may further include identify the first subject based on the at least one identification physiological feature.

For illustration purposes, the disclosure describes systems and methods for identification system. It should be noted that the identification system 100 described below is merely provided for illustration purposes, and not intended to limit the scope of the present disclosure.

Figure 1:
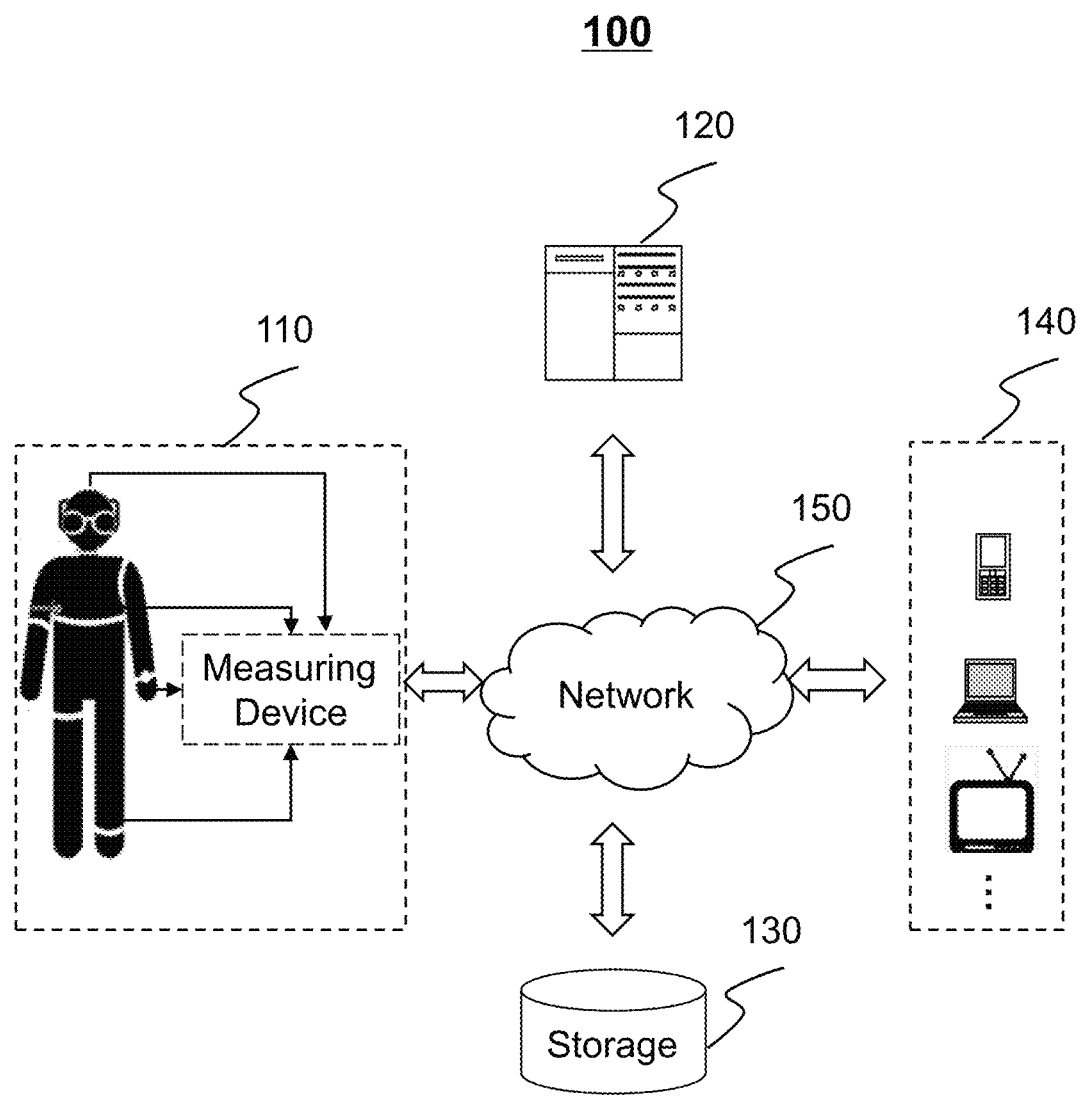
FIG. 1 is a schematic diagram illustrating an exemplary identification system according to some embodiments of the present disclosure.

FIG. 1 is a schematic diagram illustrating an exemplary identification system 100 according to some embodiments of the present disclosure. As shown, the identification system 100 may include a measuring device 110, a processing engine 120, a storage 130, a terminal 140, and a network 150. In some embodiments, the measuring device 110, the processing engine 120, the storage 130, and/or the terminal 140 may be connected to and/or communicate with each other via a wireless connection (e.g., the network 150), a wired connection, or a combination thereof. The connection between the components in the identification system 100 may be variable. Merely by way of example, the measuring device 110 may be connected to the processing engine 120 through the network 150, as illustrated in FIG. 1. As another example, the measuring device 110 may be connected to the processing engine 120 directly. As a further example, the storage 130 may be connected to the processing engine 120 through the network 150, as illustrated in FIG. 1, or connected to the processing engine 120 directly. As still a further example, the terminal 140 may be connected to the processing engine 120 through the network 150, as illustrated in FIG. 1, or connected to the processing engine 120 directly.

The measuring device 110 may measure a physiological signal. The physiological signal may relate to or be used to determine or estimate physiological features of interest. In some embodiments, the physiological signal may include a physiological electrical signal and a physiological non-electrical signal. Exemplary physiological electrical signals may include a photoplethysmogram (PPG) signal, an electrocardiogram (ECG) signal, an electroencephalogram (EEG) signal, an electromyogram (EMG) signal, or the like, or a combination thereof. Exemplary physiological non-electrical signals may include a respiration signal, a blood pressure, a blood oxygen saturation signal, or the like, or a combination thereof. The physiological features may be one or more spatial, temporal, spectral, and/or personal properties associated with the physiological signal. For example, the physiological features may include a pulse transit time (PTT), a pulse transit time variation (PTTV), a blood pressure (BP), a systolic blood pressure (SBP), a diastolic blood pressure (DBP), a pulse rate, a heart rate, a HRV, cardiac murmur, blood oxygen saturation, a blood density, a blood oxygen level, or the like, or any combination thereof.

The measuring device 110 may include, for example, a clinical device, a household device, a portable device, a wearable device, or the like, or a combination thereof. As used herein, a clinical device may be one that meets applicable standards and/or specifications to be used in a clinical setting including, for example, a hospital, a doctor's office, a nursing home, or the like. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses, a shoulder strap, a smart watch, an anklet, a thigh band, an armband, a chest belt, a necklet, a finger clip, or the like, or a combination thereof. The above mentioned examples of measuring device 110 are provided for illustration purposes, and not intended to limit the scope of the present disclosure. The measuring device 110 may be in another form including, for example, a fingerstall, a wristband, a brassiere, an underwear, a chest band, or the like, or a combination thereof.

Merely by way of example, the measuring device 110 may include a wearable or portable device that may measure one or more cardiovascular signals. In some embodiments, the wearable or portable device may process at least some of the measured signals, estimate a physiological feature of interest based on the measured signals, display a result including the physiological feature of interest in the form of, for example, an image, an audio alert, perform wired or wireless communication with another device or server, or the like, or a combination thereof. In some embodiments, the wearable or portable device may communicate with another device (for example, the terminal 140) or a server (for example, a cloud server). The device or server may process at least some of the measured signals, estimate a physiological feature of interest based on the measured signals, display a result including the physiological feature of interest in the form of, for example, an image, an audio alert, or the like, or a combination thereof.

In some embodiments, the operations of processing the measured signals, estimating a physiological feature, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject whose signal is measured or a physiological feature of interest is estimated or monitored. As used herein, a subject may refer to a person or animal whose signal or information is acquired and whose physiological feature is acquired, estimated, or monitored. Merely by way of example, a subject may be a patient whose physiological signals are acquired. Merely by way of example, the subject wears the measuring device 110 that may measure one or more physiological signals; the measured one or more physiological signals are transmitted to a smart phone that may calculate or estimate one or more physiological features of interest based on the measured signals. The calculated one or more physiological features related to the subject may be input a personalized model for the subject, and the identification of the subject may be determined based on the one or more physiological features and the personalized model for the subject.

In some embodiments, the measuring device 110 may include various types of sensors including, for example, an electrode sensor, an optical sensor, a photoelectric sensor, a pressure sensor, an accelerometer, a gravity sensor, a temperature sensor, a moisture sensor, or the like, or a combination thereof. The measuring device may monitor and/or detect one or more types of variables related to the subject including, for example, weight, temperature, humidity, user or subject input, or the like, or a combination thereof. The measuring device 110 may also include a positioning system, for example, a GPS receiver, or a location sensor, and the position information may be transmitted to the processing engine 120, the storage 130, the terminal 140, or the like, or a combination thereof, through the network 150. The position information and measured signals may be transmitted simultaneously or successively.

The processing engine 120 may process data and/or information obtained from the measuring device 110, the storage 130, and/or the terminal 140. In some embodiments, the processing engine 120 may identify a subject based on a physiological signal relating to the subject. In some embodiments, the processing engine 120 may register a subject by determining an identification physiological feature based on a physiological signal relating to the subject. For example, the processing engine 120 may extract one or more physiological features from the physiological signal relating to the subject obtained from the measuring device 110. The processing engine 120 may generate one or more models based on multiple physiological features relating to the subject. The processing engine 120 may also determine the identification physiological feature based on the models and the physiological features relating to the subject. In some embodiments, the processing engine 120 may be a single server or a server group. The server group may be centralized or distributed. In some embodiments, the processing engine 120 may be local or remote. For example, the processing engine 120 may access information and/or data from the measuring device 110, the storage 130, and/or the terminal 140 via the network 150. As another example, the processing engine 120 may be directly connected to the measuring device 110, the terminal 140, and/or the storage 130 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 120 may be implemented by a computing device 200 having one or more components as described in connection with FIG. 2.

The storage 130 may store data, instructions, and/or any other information. In some embodiments, the storage 130 may store data obtained from the measuring device 110, the processing engine 120, and/or the terminal 140. The data may include a physiological signal, a physiological feature, a model applied in data processing, a personalized data, or other data generated in a process for identifying a subject. In some embodiments, the personalized data may include static data, dynamic data, or both. Exemplary static data may include various information regarding a subject including gender, age, weight, height, contact information, birthday, a health history (for example, whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (for example, a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, or the like, or a combination thereof.

In some embodiments, the storage 130 may store data and/or instructions that the processing engine 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the identification system 100 (e.g., the processing engine 120, the terminal 140, etc.). One or more components in the identification system 100 may access the data or instructions stored in the storage 130 via the network 150. In some embodiments, the storage 130 may be part of the processing engine 120.

The terminal 140 may be connected to and/or communicate with the measuring device 110, the processing engine 120, and/or the storage 130. For example, the processing engine 120 may acquire an instruction inputted from the terminal 140 via a user. As another example, the terminal 140 may obtain physiological data from the measuring device 110, the processing engine 120, and/or the storage 130. In some embodiments, the terminal 140 may include a mobile device, a tablet computer, a laptop computer, or the like, or a combination thereof. For example, the mobile device may include a mobile phone, a personal digital assistance (PDA), a gaming device, a navigation device, a point of sale (POS) device, a laptop, a tablet computer, a desktop, or the like, or a combination thereof. In some embodiments, the terminal 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal 140 may be part of the processing engine 120.

In some embodiments, the terminal 140 in the system 100 may be configured for processing at least some of the measured signals, estimating a physiological feature of interest based on the measured physiological signals, displaying a result including the physiological feature of interest in the form of, for example, an image, storing data, controlling access to the system 100 or a portion thereof (for example, access to the personal data stored in the system 100 or accessible from the system 100), managing input-output from or relating to a subject, or the like, or a combination thereof. Other devices may include a device that may work independently, or a processing unit or processing module assembled in another device (for example, an intelligent home terminal). Merely by way of example, the terminal 140 includes a CPU or a processor in the measuring device 110. In some embodiments, the terminal 140 may include a mobile device 300 as described in FIG. 2.

The network 150 may include any suitable network that can facilitate exchange of information and/or data for the identification system 100. In some embodiments, one or more components of the identification system 100 (e.g., the measuring device 110, the processing engine 120, the storage 130, the terminal 140, etc.) may communicate information and/or data with one or more other components of the identification system 100 via the network 150. For example, the processing engine 120 may obtain image data from the measuring device 110 via the network 150. As another example, the processing engine 120 may obtain user instruction(s) from the terminal 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the identification system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. As another example, the processing engine 120 and the terminal 140 may be integrated into one single device. However, those variations and modifications do not depart the scope of the present disclosure.

FIG. 2 is a schematic diagram illustrating exemplary hardware and/or software components of an exemplary computing device 200 on which the processing engine 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 120 in accordance with techniques described herein. The computer instructions may include, for example, routines, programs, objects, components, data structures, procedures, modules, and functions, which perform particular functions described herein. For example, the processor 210 may process physiological data obtained from the measuring device 110, the storage 130, terminal 140, and/or any other component of the identification system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the measuring device 110, the storage 130, the terminal 140, and/or any other component of the identification system 100. In some embodiments, the storage 220 may include a mass storage, a removable storage, a volatile read-and-write memory, a read-only memory (ROM), or the like, or a combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 120 for identifying a subject.

The I/O 230 may input and/or output signals, data, information, etc. In some embodiments, the I/O 230 may enable a user interaction with the processing engine 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing engine 120 and the measuring device 110, the storage 130, and/or the terminal 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
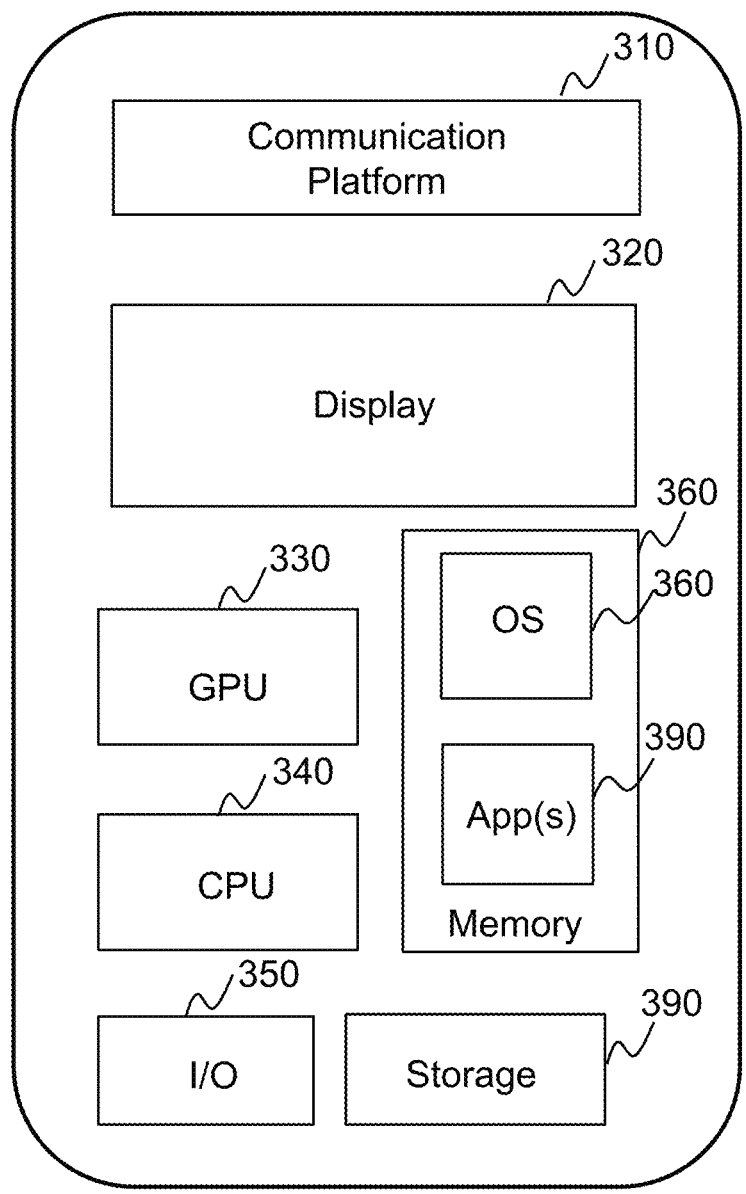
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 120. User interactions with the information stream may be achieved via the I/O 350 and provided to the processing engine 120 and/or other components of the identification system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
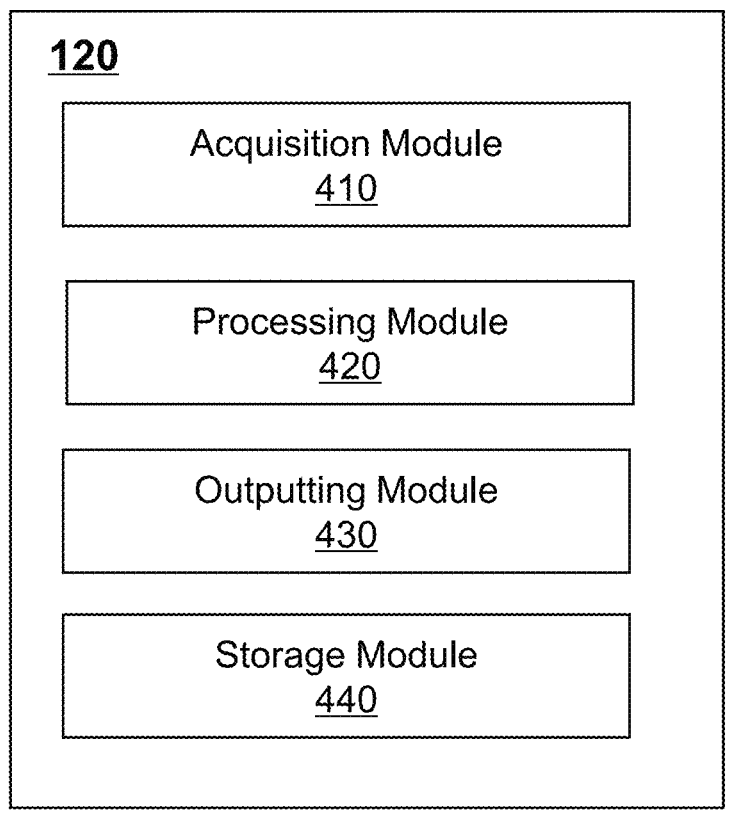
FIG. 4 is a block diagram illustrating an exemplary processing engine according to some embodiments of the present disclosure.

FIG. 4 is a block diagram illustrating an exemplary processing engine 120 according to some embodiments of the present disclosure. The processing engine 120 may include an acquisition module 410, a processing module 420, an outputting module 430, and a storage module 440. At least a portion of the processing engine 120 may be implemented on a computing device as illustrated in FIG. 2 or a mobile device as illustrated in FIG. 3.

The acquisition module 410 may be configured for acquiring a signal or information from or relating to one or more subjects. As used herein, the acquiring may be achieved by way of receiving a signal or information sensed, detected, or measured by, for example, a sensor, or by way of receiving an input from a subject or from a user other than the subject (for example, a doctor, a care provider, a family member relating to the subject, or the like, or a combination thereof). Exemplary acquired information may include physiological data. The physiological data include a photoplethysmogram (PPG) signal, an electrocardiogram (ECG) signal, a ballistocardiogram (BCG) signal, a blood pressure (BP), a systolic blood pressure (SBP), a diastolic blood pressure (DBP), a pulse rate (PR), a heart rate (HR), a heart rate variation (HRV), a cardiac murmur, a blood oxygen saturation, a density of blood, a pH value of the blood, a bowel sound, a brainwave, a fat content, a blood flow rate, or the like, or a combination thereof. Exemplary acquired information may further include information regarding a subject, for example, the height, the weight, the age, the gender, the body temperature, the arm length, the illness history, or the like, or a combination thereof.

The processing module 420 may process signal or information provided by various modules of the processing engine 120. In some embodiments, the processing module 420 may register a subject. For example, the processing model 420 may determine one or more identification physiological features by processing physiological signals relating to the subject. In some embodiments, the processing module 420 may identify a subject based on physiological signals and identification physiological features relating to the subject. In some embodiments, the processing module 420 may be configured for performing one or more operations including, for example, a pre-processing, a calculation, a judgment, a statistical analysis, or the like, or a combination thereof. Any one of the operations may be performed based on at least some of the acquired information, or an intermediate result from another operation (for example, training data, or an operation performed by the processing module 420, or another component of the identification system 100).

The outputting module 430 may be configured for outputting acquired signal or information, for example, a physiological signal, a physiological feature of interest, a registration of a subject, an identification of a subject, or the like, or a combination thereof. For example, the outputting module 430 may output whether a first subject to be identified matches with a second subject. As another example, the outputting module 430 may output which one of multiple subjects the first subject to be identified matches with. In some embodiments, the outputting module 430 may output the acquired signal or information to the storage 130, the terminal 140, and/or any other storage. As used herein, a module may have an independent processor, or use system shared processor(s). The processor(s) may perform functions according to instructions related to various modules. For example, the processing module 420, according to relevant instructions, may retrieve acquired signals and perform calculations to obtain one or more physiological feature of interest.

The storage module 440 may store information. The information may include programs, software, algorithms, data, text, number, images and some other information. For example, the information may include physiological signals, physiological features, models, or the like, or a combination thereof. In some embodiments, the storage module 440 may store program(s) and/or instruction(s) that can be executed by the processor(s) of the processing engine 120 to acquire data, determine imaging parameters, reconstruct MR images, and/or display any intermediate result or a resultant image.

In some embodiments, one or more modules illustrated in FIG. 5 may be implemented in at least part of the exemplary identification system 100 as illustrated in FIG. 1. For example, the acquisition module 410, the outputting module 430, the processing module 420, and/or the storage module 440 may be integrated into a console (not shown). Via the console, a user may set parameters for identifying a subject, controlling identification processes, etc. In some embodiments, the console may be implemented via the processing engine 120 and/or the terminal 140.

FIG. 5 is a block diagram illustrating an exemplary processing module 420 according to some embodiments of the present disclosure. The processing module 420 may include a registration unit 520, an identification unit 540, and a storage unit 560. At least a portion of the processing module 420 may be implemented on a computing device as illustrated in FIG. 2 or a mobile device as illustrated in FIG. 3.

The registration unit 520 may be configured to register a subject. In some embodiments, the registration of the subject may include determining one or more identification features relating to the subject and/or store the one or more identification features and/or any other identification information relating to the subject in, for example, the storage 130, the terminal 140, the storage module 440, and/or any other storage. In some embodiments, the registration unit 520 may further include a first feature extraction sub-unit 522, a model generation sub-unit 524, and an identification information determination sub-unit 526. The first feature extraction sub-unit 522 may be configured to extract one or more physiological features for training a model. The model generation sub-unit 524 may be configured to generate one or more models. In some embodiments, the models may be configured to determine one or more identification physiological features relating to a subject to be registered. In some embodiments, the model may be configured to identify and/or classify the subject to be registered based on the identification physiological features. The identification information determination sub-unit 526 may determine identification information relating to a subject. In some embodiments, the identification information may include one or more identification physiological features, personalized data, and/or other identification information relating to a subject (e.g., a fingerprint, a DNA, an iris, etc.).

The identification unit 540 may be configured to identify a subject to be identified. In some embodiments, the identification unit 540 may further include a second feature extraction sub-unit 542, a judgment sub-unit 544 and a calculation sub-unit 546. The second feature extraction sub-unit 542 may extract physiological features relating to a subject to be identified. The judgment sub-unit 544 may determine whether a subject to be identified matches with a registration subject. The calculation sub-unit 546 may perform a calculation function in a process of, for example, identifying a subject to be identified. For example, the calculation sub-unit 546 may determine a difference between a subject to be identified and a registration subject.

The storage unit 560 may store information including, for example, information for identifying a subject and/or registering a subject. The information may include programs, software, algorithms, data, text, number, and some other information. For example, the storage unit 560 may store identification features determined by the registration unit 520, one or more models generated by the model generation sub-unit 524, etc. In some embodiments, the storage unit 560 may store a condition, a threshold, or a standard for identifying a subject. The storage unit 560 may store intermediate results and/or final results in the process of a subject identification or registration.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the first feature extraction sub-unit and the second feature extraction sub-unit may be integrated into one single unit. As another example, the processing module 420 may further include a preprocessing unit.

Figure 6:
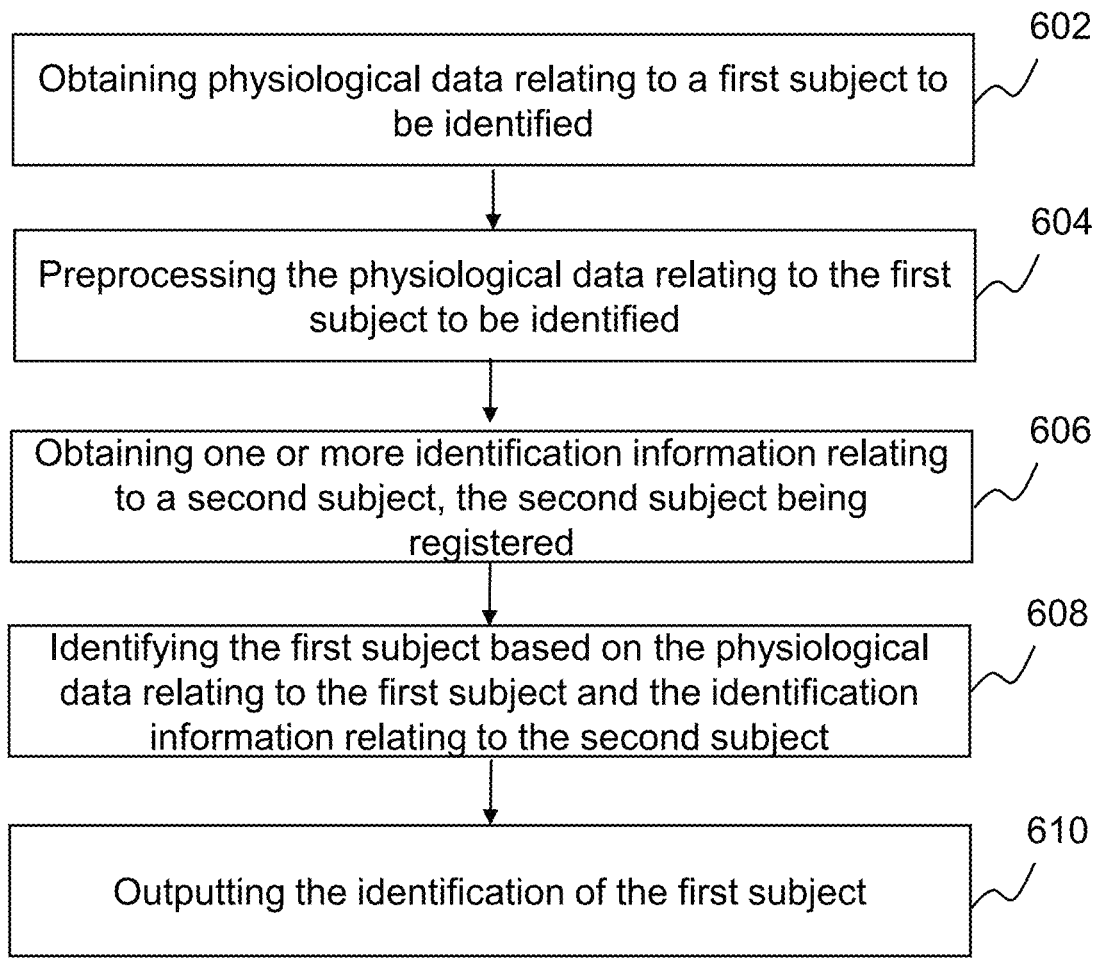
FIG. 6 is a flowchart illustrating an exemplary process for identifying a subject according to some embodiments of the present disclosure.

FIG. 6 is a flowchart illustrating an exemplary process 600 for identifying a subject according to some embodiments of the present disclosure. In some embodiments, one or more operations of process 600 illustrated in FIG. 6 may be implemented in the identification system 100 illustrated in FIG. 1. For example, the process 600 illustrated in FIG. 6 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3).

In 602, physiological data relating to a first subject to be identified may be obtained. Operation 602 may be performed by the acquisition module 410. In some embodiments, the physiological data may include one or more physiological signals relating to the first subject, such as a photoplethysmogram (PPG) signal, an electrocardiogram (ECG) signal, a ballistocardiogram (BCG) signal, a phonocardiogram (PCG) signal, an impedance cardiogram (ICG) signal, a blood pressure (BP), a systolic blood pressure (SBP), a diastolic blood pressure (DBP), a pulse rate (PR), a heart rate (HR), a heart rate variation (HRV), a cardiac murmur, a blood oxygen saturation, a density of blood, a pH value of the blood, a bowel sound, a brainwave, a fat concentration, a blood flow rate, or the like, or a combination thereof. The physiological signals mentioned above may be time dependent. In some embodiments, the physiological signals may be a single temporal signal of certain length, for example, a PPG signal lasting 200 seconds.

In some embodiments, the physiological data may further include personalized data relating to the first subject, such as age, height, weight, gender, health history, etc., as described elsewhere in the present disclosure. See for example, FIG. 1 and descriptions thereof. In some embodiments, the physiological data relating to the first subject to be identified may be obtained from the measuring device 110, the storage 130, the terminal 140, and/or other external storages connected to the identification system 100. For example, the acquisition module 410 may obtain a physiological signal (e.g., a PPG signal) relating to the first subject to be identified from the measuring device 110.

In 604, the physiological data may be preprocessed. Operation 604 may be performed by the processing model 420. In some embodiments, the preprocessing of the physiological data may include a denoising operation, a normalization operation, or the like, or a combination thereof. The denoising operation may be performed to reduce or remove noise or errors in the physiological data. The denoising operation may be performed based on, for example, a wavelet transform, a Fourier transform, a discrete wavelet transform (DWT), an orthogonal wavelet transform (Mallat), a Hilbert-Huang transform, or any other mathematical transform. In some embodiments, the denoising operation may be performed by using a filtering technique. Exemplary filtering techniques may include a smoothing filtering algorithm, an adaptive filtering algorithm, a band stop filtering algorithm, a Levkov filtering algorithm, a low-pass filtering algorithm, a band-pass filtering algorithm, a median filtering algorithm, a morphological filtering algorithm, a curve fitting, or the like, or a combination thereof. During the process of the preprocessing, the techniques and/or algorithms mentioned herein may be used in parallel or may be used in combination. Additionally, real-time transformation of time domain or frequency domain may also be implemented in 604, and the signals or related information may be used in time domain, frequency domain, wavelet domain, or all of them.

Figure 7:
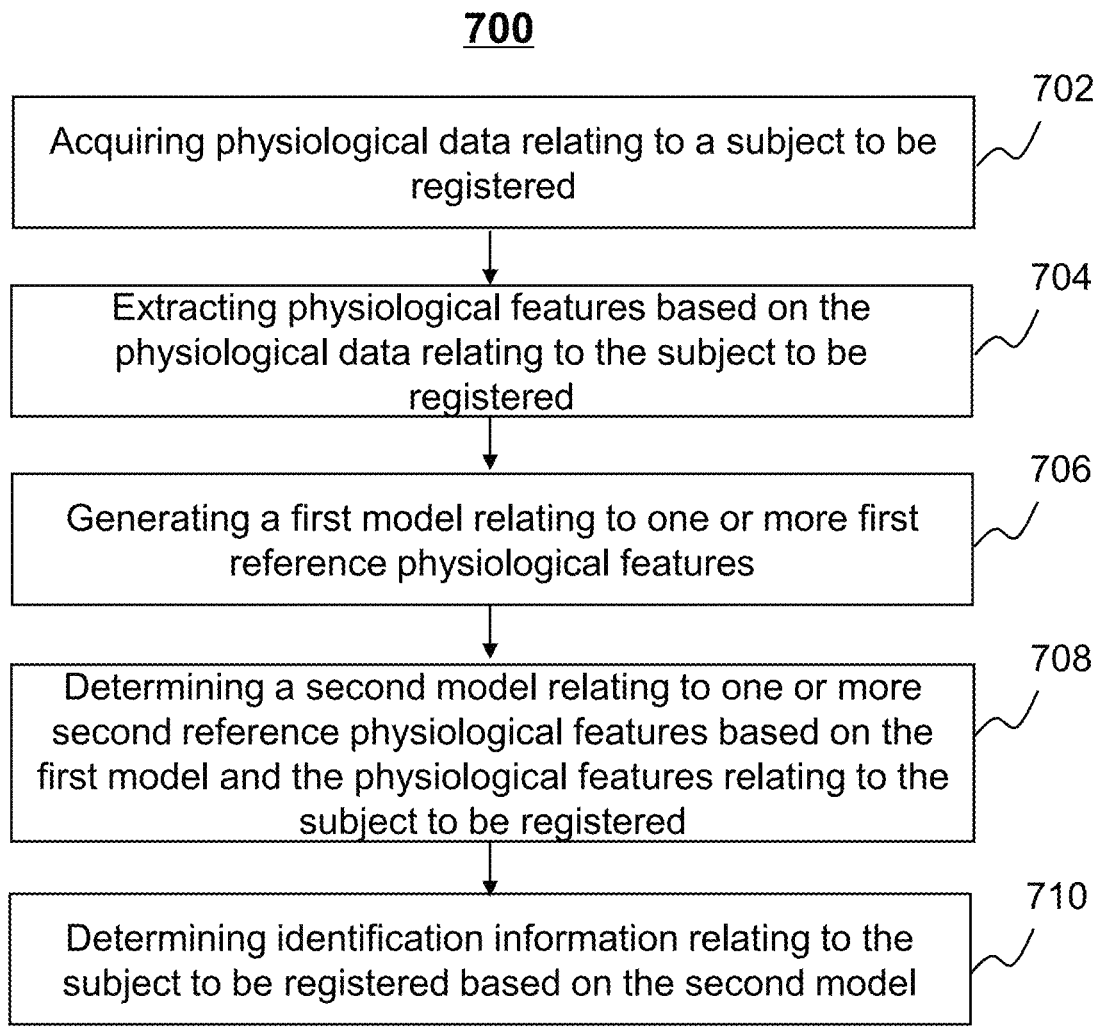
FIG. 7 is a flowchart illustrating an exemplary process for determining identification information relating to a subject to be registered according to some embodiments of the present disclosure.

In 606, identification information relating to a second subject may be obtained. Operation 606 may be performed by the acquisition module 410. In some embodiments, the identification information relating to the second subject may be obtained from the storage 130, the terminal 140, and/or any other storage. For example, the identification information relating to the second subject may be predetermined by and/or stored in the identification system by. In some embodiments, the identification information may include one or more identification physiological features, personalized data relating to the second subject, and/or other information relating to an identification of the second subject (e.g., a DNA, a fingerprint, a voice, an iris, etc.). The identification physiological features relating to the second subject may be determined based on the physiological data relating to the second subject (e.g., physiological signals,) according to process 700 as illustrated in FIG. 7. In some embodiments, the second subject may be registered. As used herein, the registration of the second subject may refer to determine one or more identification physiological features relating to the second subject that may be used to identify the second subject and/or store the identification physiological features and/or other personalized data relating to the second subject in, for example, the storage 130, the terminal 140, the storage module 440, and/or other external storages that may be accessed by the identification system 100. In some embodiments, the physiological data relating to the first subject to be identified and the identification physiological features relating to the second subject may be acquired simultaneously, at or around the same time. In some embodiments, one signal may be acquired prior to the other signal.

Figure 9:
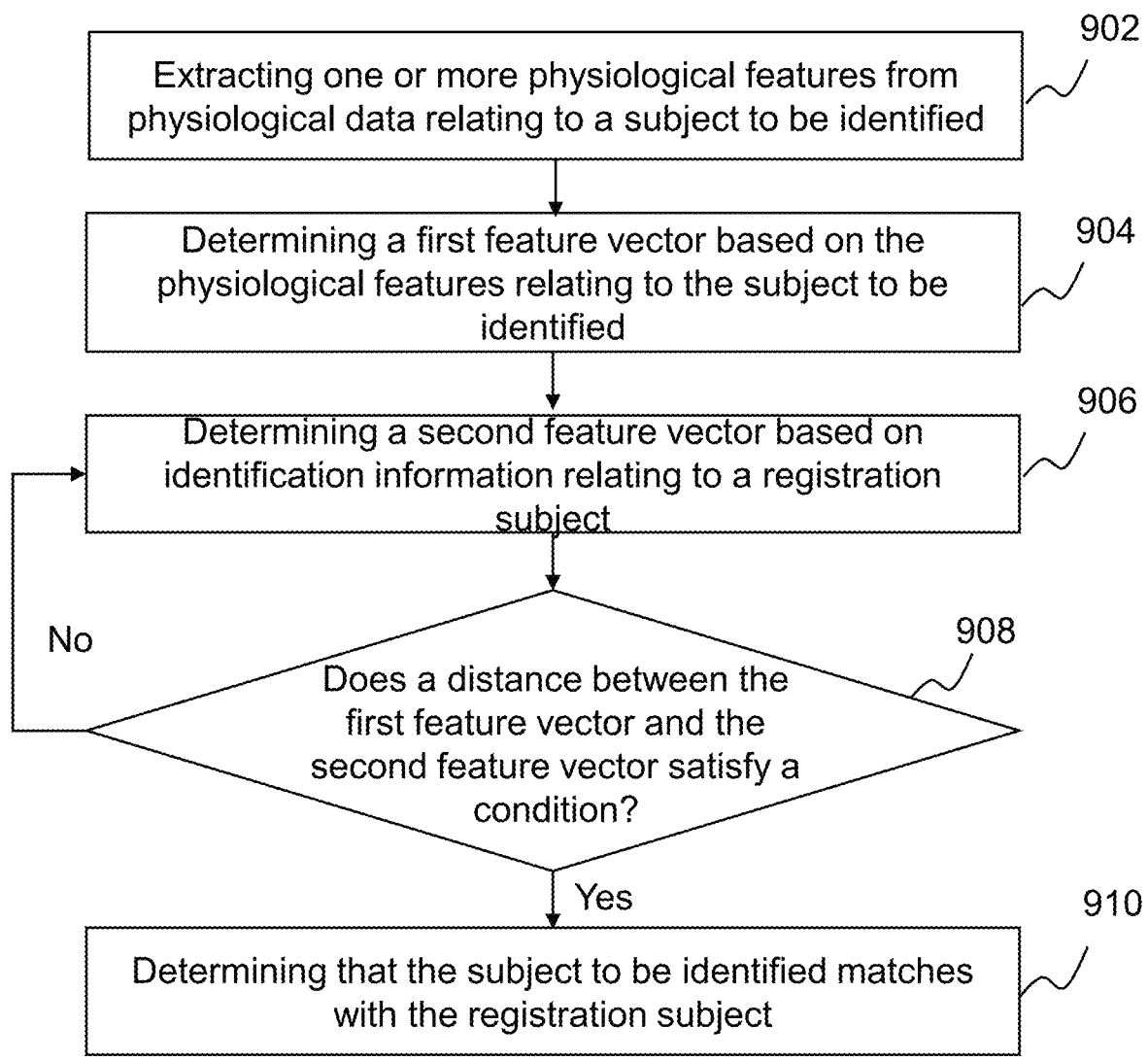
FIG. 9 is a flowchart illustrating an exemplary process for identifying a subject based on a physiological signal according to some embodiments of the present disclosure orientation information of image data according to some embodiments of the present disclosure.

In 608, the first subject may be identified based on the physiological data relating to the first subject and the identification information relating to the second subject. Operation 608 may be performed by the processing module 420. In some embodiments, multiple physiological features may be extracted from the physiological data relating to the first subject. For example, physiological features (e.g., PTT) corresponding to a PPG signal may be extracted. In some embodiments, at least one of the multiple physiological features of the first subject to be identified may be compared with that of the second subject according to process 900 as illustrated in FIG. 9. The first subject to be identified may be identified by determining whether the first subject to be identified is matched with the second subject based on the comparison. In some embodiments, at least one of the multiple physiological features of the first subject to be identified may be compared with that of multiple second subjects. The first subject to be identified may be identified by determining that which one of the multiple second subjects is matched with the first subject to be identified based on the multiple comparisons.

In 608, the identification of the first subject to be identified may be outputted. Operation 608 may be performed by the outputting module 430. In some embodiments, the identification of the subject to be identified may be outputted to the storage 130, the terminal 140, the storage module 440, and/or any other external device. For example, the identification of the subject to be identified may be transmitted to the terminal 140 (e.g., a computer) for display. In some embodiments, the identification of the first subject may include whether the first subject matches with the second subjects (e.g., Yes or No). In some embodiments, the identification of the first may include a probability of the first subject matching with the second subject. In some embodiments, the identification of the first subject if the first subject matching with the second subject may further include personalized data relating to the second subject, such as a ID number, a blood type, an address, a health history, age, or the like, or a combination thereof.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 608 may be unnecessary. As another example, operations 602 and 604 may be performed simultaneously.

FIG. 7 is a flowchart illustrating an exemplary process 700 for determining identification information relating to a subject to be registered according to some embodiments of the present disclosure. In some embodiments, one or more operations of process 700 illustrated in FIG. 7 may be implemented in the identification system 100 illustrated in FIG. 1. For example, the process 700 illustrated in FIG. 7 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3). Operation 604 may be performed according to process 700.

In 702, physiological data relating to a subject to be registered may be acquired. Operation 702 may be performed by the acquisition module 410. In some embodiments, the physiological data relating to the subject to be registered may include one or more physiological signals relating to the subject to be registered, such as a photoplethysmogram (PPG) signal, an electrocardiogram (ECG) signal, a ballistocardiogram (BCG) signal, a phonocardiogram (PCG) signal, an impedance cardiogram (ICG) signal, a blood pressure (BP), a systolic blood pressure (SBP), a diastolic blood pressure (DBP), a pulse rate (PR), a heart rate (HR), a heart rate variation (HRV), a cardiac murmur, a blood oxygen saturation, a density of blood, a pH value of the blood, a bowel sound, a brainwave, a fat content, a blood flow rate, or the like, or a combination thereof. In some embodiments, the physiological data may include personalized data relating to the subject to be registered, such as age, height, weight, gender, heath history, etc., as described elsewhere in the present disclosure. See for example, FIG. 1 and descriptions thereof. In some embodiments, the physiological data relating to the subject to be registered may be obtained from the measuring device 110, the storage 130, the terminal 140, and/or other external storage connected to the identification system 100. For example, the acquisition module 410 may obtain the physiological signal relating to the subject to be registered (e.g., a PPG signal) from the measuring device 110.

In 704, physiological features may be extracted from the physiological data relating to the subject to be registered. Operation 704 may be performed by the first feature extraction sub-unit 522. In some embodiments, the physiological features corresponding to the physiological signal may include waveform features, feature points, or other features determined based on the feature points and/or the waveform features. For example, a waveform feature corresponding to an ECG signal may include a P wave, a QRS wave, a T wave, an R wave, etc., in a cardiac cycle. As another example, a waveform feature corresponding to a PPG signal may include a P wave, a V wave, etc. The feature points may include a peak point, a starting point, an ending point, a minimum point, a maximum point, an inflection point, etc. For example, the feature point corresponding to a PPG wave may include a starting point of the PPG wave, an ending point of the PPG wave, a peak of the PPG wave, a front valley of the PPG wave, a tidal wave of the PPG wave, etc. In some embodiments, the waveform feature may be determined based on the feature points. For example, a starting of the waveform, an ending of the waveform, a slope of the waveform, an amplitude of the waveform, etc., may be determined based on the feature points. In some embodiments, the feature points may be further extracted from a first-order derivative of a physiological signal, a second-order derivative of a physiological signal, a third-order derivative of a physiological signal, etc.

In some embodiments, the physiological features may further include time intervals, a phase, frequencies, cycles, a ratio, a maximum slope, a starting time, an ending time, a direct current (DC) component, an alternating current (AC) component, or the like, or any combination thereof, of a function of a waveform (e.g., a PPG waveform, an ECG waveform, etc.). The function of the waveform may be identical function, or the first derivative or higher order derivatives of the waveform. For example, one feature point may be a peak or a valley of a physiological signal, e.g., the peak or valley of R wave of an ECG signal, a fastest rising point of a PPG signal, a higher order moment or a higher order derivative of the PPG signal, a pulse area of the PPG signal, a maximum positive peak of S2 of a PCG signal, or a peak of an ICG signal, or the like. In some embodiments, the physiological features may further include a wave intensity, a blood pressure, a heart rate, a respiratory rate, etc.

In some embodiments, a portion of the physiological features (e.g., the blood pressure, the heart rate, the respiratory rate, etc.,) may be obtained from the measuring device 110, the terminal 140, the storage 130, or other storage. In some embodiments, the portion of the physiological features (e.g., the blood pressure, the heart rate, the respiratory rate, etc.,) may be determined or estimated based one or more other physiological features. For example, physiological features corresponding to a PPG signal (e.g., an amplitude difference between adjacent P wave and V wave (hvp), a time interval between two adjacent P waves (tpp), a time interval between two adjacent V waves (tvv), a time interval between adjacent P wave and V wave (tvp), etc.) may be determined based on one or more feature points relating to the PPG signal. As another example, a PTT may be estimated based on a time interval between a wave peak (or wave trough) of a PPG wave and a R wave of an ECG wave. As still an example, a heart rate may be estimated based on a time interval between adjacent waves. As a further example, SpO2 may be estimated based on an intensity of a wave peak and a wave trough.

In 706, a first model relating to one or more first reference physiological features may be generated. Operation 706 may be performed by the model generation sub-unit 524. In some embodiments, the first model may be configured to determine at least one portion of physiological features (also referred to as effective physiological features) relating to an object (e.g., the subject to be registered in 702). The effective physiological features may correspond to the first reference physiological features. As used herein, the effective physiological features may be used to identify the object (e.g., the subject to be registered in 702). For example, the physiological features relating to the subject to be registered extracted in 702 may be inputted into the first model. The first model may determine effective physiological features relating to the subject to be registered corresponding to the first reference physiological features. In some embodiments, the first model may be configured to identify an object (e.g., the subject to be registered in 702) based on the one or more first reference physiological features. For example, physiological features relating to a first subject to be identified and physiological features relating to a second subject may be inputted into the first model. The effective physiological features relating to the first subject corresponding to the first reference physiological features may be used by the first model to identify the first subject. The first model may determine whether the first subject matches with the second subject or a possibility that the first subject matches with the second subject.

In some embodiments, the first reference physiological features may relate to types of multiple physiological features. For example, the first reference physiological features may include one or more types of physiological features (e.g., PTT) relating to a physiological signal, such as a PPG signal, an ECG signal, etc. In some embodiments, the first reference physiological features may relate to a relationship between at least two types of physiological signals, such as a physiological electronic signal and a physiological non-electronic signal. For example, the first reference physiological features may relate to a relationship between a blood pressure signal and a PPG signal and/or an ECG signal.

In some embodiments, the first model may be generated based on a machine learning technique. The machine learning technique according to a learning mechanism may include a supervised learning, an unsupervised learning, a semi-supervised learning, reinforcement learning, or the like, or a combination thereof. In some embodiments, the machine learning technique may include a regression algorithm, a case learning algorithm, a formal learning algorithm, a decision tree learning algorithm, a Bayesian learning algorithm, a kernel learning algorithm, a clustering algorithm, an association rules learning algorithm, a neural network learning algorithm, a deep learning algorithm, a dimension reduction algorithm, etc. The regression algorithm may include a logistic regression algorithm, a stepwise regression algorithm, a multivariate adaptive regression splines algorithm, a locally estimated scatterplot smoothing algorithm, etc. The case learning algorithm may include a k-nearest neighbor algorithm, a learning vector quantization algorithm, a self-organizing map algorithm, etc. The formal learning algorithm may include a ridge regression algorithm, a least absolute shrinkage and selection operator (LAASSO) algorithm, an elastic net algorithm, etc. The decision tree learning algorithm may include a classification and regression tree algorithm, an iterative dichotomiser 3 (ID3) algorithm, a C4.5 algorithm, a chi-squared automatic interaction detection (CHAID) algorithm, a decision stump algorithm, a random forest algorithm, a mars algorithm, a gradient boosting machine (GBM) algorithm, etc. The Bayesian learning algorithm may include a naive Bayesian algorithm, an averaged one-dependence estimators algorithm, a Bayesian belief network (BBN) algorithm, etc. The kernel learning algorithm may include a support vector machine algorithm, a linear discriminate analysis algorithm, etc. The neural network learning algorithm may include a perceptron neural network algorithm, a back propagation algorithm, a Hopfield network algorithm, a self-organizing map (SOM) algorithm, a learning vector quantization algorithm, etc. The deep learning algorithm may include a restricted Boltzmann machine algorithm, a deep belief networks (DBN) algorithm, a convolutional neural network (CNN) algorithm, a stacked auto-encoders algorithm, a long-short term memory (LSTM) algorithm, a generative adversarial network (GAN) algorithm, etc. The dimension reduction algorithm may include a principle component analysis algorithm, a partial least square regression algorithm, a Sammon mapping algorithm, a multi-dimensional scaling algorithm, a projection pursuit algorithm, etc.

In some embodiments, a machine learning algorithm may correspond to a machine learning model. The first model may be generated by training a first machine learning model based on a first set of training data. The first set of training data may include a first set of physiological features. The first set of physiological features may be extracted from multiple physiological signals relating to multiple samples. In some embodiments, the first set of training data may further include multiple personalized data corresponding to the multiple samples, such as ages, genders, weights, heights, medical histories, or other information relating to the samples as described elsewhere in the present disclosure. In some embodiments, the first set of physiological features or multiple physiological signals relating to the multiple samples may be acquired from the storage 130, the terminal 140, or any other external data source or storage that the identification system 100 may be connected to.

In 708, a second model relating to one or more second reference physiological features may be generated based on the first model and the physiological features relating to the subject to be registered. Operation 708 may be performed by the model generation sub-unit 524. In some embodiments, the second model may be configured to determine at least one portion of physiological features (also referred to as identification physiological features or personalized physiological features) relating to an object (e.g., the subject to be registered in 702). The identification physiological features may correspond to the second reference physiological features. The identification physiological features may be configured to identify the object (e.g., the subject to be registered in 702). For example, the physiological features relating to the subject to be registered extracted in 702 may be inputted into the second model. The second model may determine identification physiological features relating to the subject to be registered corresponding to the second reference the physiological features. In some embodiments, the second model may be configured to identify an object (e.g., the subject to be registered in 702) based on the one or more second reference physiological features. For example, physiological features relating to a first subject to be identified and physiological features relating to a second subject may be inputted into the second model. Identification physiological features relating to the first subject corresponding to the second reference physiological features and identification physiological features relating to the second subject corresponding to the second reference physiological features may be determined by the second model. The second model may compare the identification physiological features relating to the first subject and the identification physiological features relating to the second subject. The second model may determine whether the second subject matches with the first subject or a probability that the first subject matches with the second subject. The second model may determine which one of multiple second subjects the first subject matches with or possibilities that the first subject matches with each of the multiple second subjects when multiple second subjects are compared with the first subject.

In some embodiments, the second model may be personalized. One object (e.g., the subject to be identified) may correspond to a second model. The second reference physiological features relating to the second model may be different for different objects. The second model of the subject to be registered in 702 may be generated by training the first model based on a second set of training data relating to the subject to be registered. The second set of training data relating to the subject to be registered may include a second set of physiological features relating to the subject to be registered. In some embodiments, the second set of physiological features may include the physiological features relating to the subject to be registered extracted in 704. In some embodiments, the second set of physiological features may include the effective physiological features relating to the subject to be registered determined based on the first model. In some embodiments, the second set of training data may further include multiple personalized data relating to the subject to be registered, such as age, gender, weight, height, medical history, or other information relating to the samples as described elsewhere in the present disclosure. In some embodiments, the second model may be generated by training a machine learning model as described elsewhere in the disclosure based on the second set of physiological features relating to the subject to be registered.

In some embodiments, the second reference physiological features may relate to types of multiple physiological features. For example, the second reference physiological features may include one or more physiological features (e.g., PTT) relating to a physiological signal, such as a PPG signal, an ECG signal, etc. In some embodiments, the second reference physiological features may relate to a relationship between at least two types of physiological signals, such as a physiological electronic signal and a physiological non-electronic signal. For example, the second reference physiological features may relate to a relationship between a blood pressure signal and a PPG signal and/or an ECG signal. Furthermore, a second model relating to the second reference physiological features indicating a relationship between at least two types of physiological signals may be determined according to follow operations. A third model may be generated by training a machine learning model as described elsewhere in the disclosure based on a third set of training data. The third set of training data may be determined based on at least two types of physiological signals relating to multiple samples (e.g., PPG signals and blood pressure signals). Then the third model may be trained by a fourth set of training data. The fourth set of training data may be determined based on at least two types of physiological signals (e.g., PPG signals and blood pressure signals) relating to the object (e.g., the subject to be registered in 702). The second model relating to the object (e.g., the subject to be registered in 702) may be generated by based on the trained third model.

In 710, identification information relating to the subject to be registered may be determined based on the second model. Operation 710 may be performed by the identification information determination sub-unit 526. In some embodiments, the identification information relating to the subject to be registered may include one or more identification physiological features. In some embodiments, the identification physiological features relating to the subject to be registered may be determined by processing the physiological features extracted in 704 via the second model. In some embodiments, the identification physiological features relating to the subject to be registered may be determined by processing the effective physiological features determined based on the first model via the second model. In some embodiments, the identification information may include the second model of the subject to be registered. For example, the second model may be used to identify the subject to be registered. The second model may be personalized corresponding to the subject to be registered. Furthermore, the physiological features relating to the subject to be registered extracted in 702 may be inputted to the second model. At least one portion of the physiological features relating to the subject to registered extracted in 702 corresponding to the second reference physiological features may be determined to be used to identify the subject by the second model. In some embodiments, the subject to be registered may be determined if the at least one portion of the physiological features relating to the subject to be registered match with the second reference physiological features relating to the second model, the subject to be registered may be identified by matching with the second model. More descriptions of identifying the subject may be found in for example, process 900 as illustrated in FIG. 9.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 700 may further include preprocessing the physiological signal. As another example, operations 704 and 706 may be performed simultaneously. In some embodiments, operation 706 may be unnecessary. The identification information relating to the subject to be registered may be determined based on the first model and the physiological features relating to the subject to be registered. In some embodiments, operation 704 may be unnecessary. The second model may be generated by training a machine learning model directly based on the physiological features relating to the subject to be registered.

Figure 8:
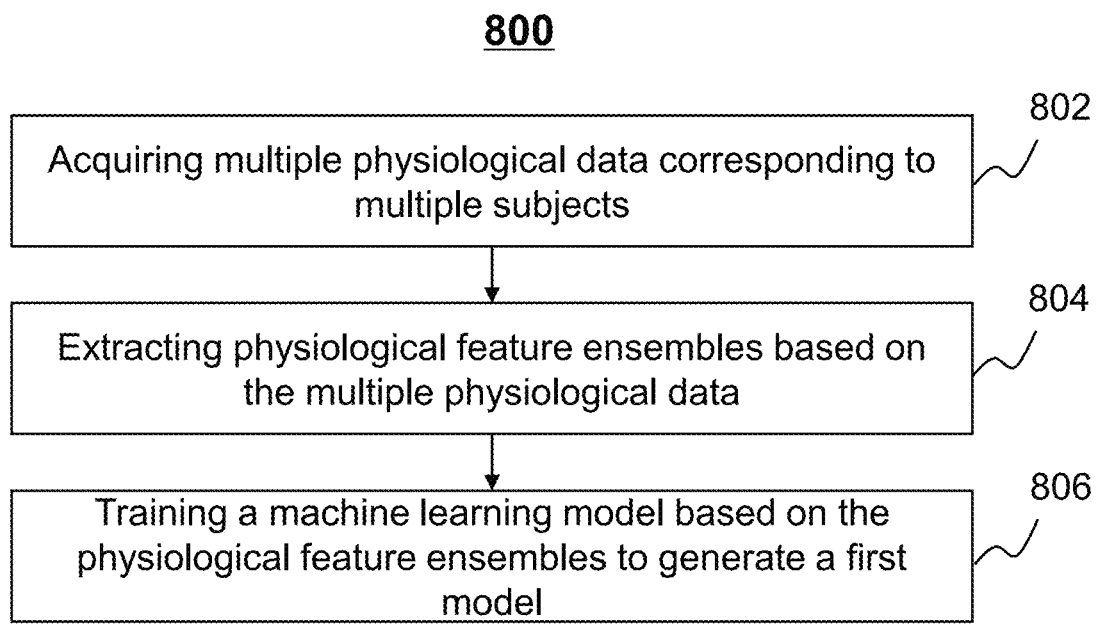
FIG. 8 is a flowchart illustrating an exemplary process for generating a first model according to some embodiments of the present disclosure.

FIG. 8 is a flowchart illustrating an exemplary process 800 for generating a first model according to some embodiments of the present disclosure. In some embodiments, one or more operations of process 800 illustrated in FIG. 8 may be implemented in the identification system 100 illustrated in FIG. 1. For example, the process 800 illustrated in FIG. 8 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3). Operation 706 may be performed according to process 800 as illustrated in FIG. 8.

In 802, multiple physiological data relating to multiple subjects may be acquired. Operation 802 may be performed by the acquisition module 410. In some embodiments, the multiple physiological data relating to the multiple subjects may obtained from the storage 130, the terminal 140, and/or any other external storage that the identification system 100 may be connected to. In some embodiments, the multiple physiological data may include physiological signals relating to the multiple signals as described elsewhere in the disclosure. For example, the physiological signals may include a physiological electronic signal (e.g., a PPG, an ECG, an EMG, etc.) and a physiological non-electronic signal (e.g., a blood pressure, a heart rate, a respiration rate, etc.) As another example, the multiple physiological data may further include personalized data corresponding to each of the multiple subjects, such as gender, age, weight, height, contact information, birthday, a health history (for example, whether a subject has a history of smoking, information regarding a prior surgery, a food allergy, a drug allergy, a medical treatment history, a history of genetic disease, a family health history, or the like, or a combination thereof), etc.

In 804, physiological feature ensembles may be extracted from the physiological data relating to the multiple subjects. Operation 804 may be performed by the first feature extraction sub-unit 522. In some embodiments, the physiological feature ensembles may be extracted according to operation 704 as illustrated in FIG. 7.

In 806, a machine learning model may be trained based on the physiological feature ensembles corresponding to the multiple subjects to generate a first model. Operation 806 may be performed by the model generation sub-unit 524. The machine learning model according to a learning mechanism may include a supervised learning model, an unsupervised learning model, a semi-supervised learning, reinforcement learning model, or the like, or a combination thereof. In some embodiments, the machine learning model may include a regression model, a case learning model, a formal learning model, a decision tree learning model, a Bayesian learning model, a kernel learning model, a clustering model, an association rules learning model, a neural network learning model, a deep learning model, a dimension reduction model, etc. The regression model may include a logistic regression model, a stepwise regression model, a multivariate adaptive regression splines model, a locally estimated scatterplot smoothing model, etc. The case learning model may include a k-nearest neighbor model, a learning vector quantization model, a self-organizing map model, etc. The formal learning model may include a ridge regression model, a least absolute shrinkage and selection operator (LAASSO) model, an elastic net model, etc. The decision tree learning model may include a classification and regression tree model, an iterative dichotomiser 3 (ID3) model, a C4.5 model, a chi-squared automatic interaction detection (CHAID) model, a decision stump model, a random forest model, a mars model, a gradient boosting machine (GBM) model, etc. The Bayesian learning model may include a naive Bayesian model, an averaged one-dependence estimators model, a Bayesian belief network (BBN) model, etc. The kernel learning model may include a support vector machine model, a linear discriminate analysis model, etc. The neural network learning model may include a perceptron neural network model, a back propagation model, a Hopfield network model, a self-organizing map (SOM) model, a learning vector quantization model, etc. The deep learning model may include a restricted Boltzmann machine model, a deep belief networks (DBN) model, a convolutional neural network (CNN) model, a stacked auto-encoders model, a long-short term memory (LSTM) model, a generative adversarial network (GAN) model, etc. The dimension reduction model may include a principle component analysis model, a partial least square regression model, a Sammon mapping v, a multi-dimensional scaling model, a projection pursuit model, etc.

In some embodiments, the first model may be generated further based on a cost function. The cost functions to select may be mean, median, standard deviation of the prediction errors of the test data. For example, the cost function may be chosen as the standard deviation of prediction error of the test data. Based on the behavior of the trained machine learning models generating in training the machine learning model, a model with minimum standard deviation of the prediction errors of the test data may be designated as the first model.

In some embodiments, the machine learning model to select may be one of the following forms:

$$\widehat{Sbp} = g_{sbp}(X_1, X_2, \ldots, X_k) + R(id)$$

$$\widehat{Dbp} = g_{dbp}(X_1, X_2, \ldots, X_k) + R(id)$$

$$\widehat{bpdiff} = g_{bpdiff}(X_1, X_2, \ldots, X_k) + R(id)$$

$$\widehat{lnSbp} = g_{lnsbp}(X_1, X_2, \ldots, X_k) + R(id)$$

$$\widehat{lnDbp} = g_{lndbp}(X_1, X_2, \ldots, X_k) + R(id)$$

Where Sbp is the systolic pressure, Dbp is the diastolic pressure. $g_{sbp}(\cdot)$, $g_{dbp}(\cdot)$, $g_{bpdiff}(\cdot)$, $g_{lnsbp}(\cdot)$, $g_{lndbp}(\cdot)$ are the structural components (non-random) of the predictive functions of the input physiological features, such as feature points of PPG signals, demographic information of the subjects, etc. The functional relationship may be linear, non-linear, regression tree or random forest which is determined by the cost function. An example of linear function takes the following form: $g(X_1, X_2, \ldots) = \beta_0 + \beta_1 X_1 + \beta_2 X_2$. $\beta i$ is the machine learning model coefficient to be determined, $x_i$ is the effective physiological features, i=1, 2, ... M, where M is the number of chosen physiological features, id is the personal variable related to the subject. The structural component $g_{sbp}(\cdot)$, $g_{dbp}(\cdot)$, $g_{bpdiff}(\cdot)$, $g_{lnsbp}(\cdot)$, $g_{lndbp}(\cdot)$ are set to be constant across general population, while R(id) denotes the random component of the predictive function, which is individual specific. In some embodiments, the structural component $g_{sbp}(\cdot)$, $g_{dbp}(\cdot)$, $g_{bpdiff}(\cdot)$, $g_{lnsbp}(\cdot)$, $g_{lndbp}(\cdot)$ may be dependent upon the training data.

In some embodiments, the first model may be configured to determine a first reference physiological features. The first reference physiological features may be used to determine effective physiological features relating to a subject that may be used to identify the subject. In some embodiments, the first reference physiological features may include types of physiological parameters relating to a physiological signal. In some embodiments, the first reference physiological features may include a relationship between at least two type physiological signals. For example, when multiple blood pressure signals and multiple PPG signals corresponding to the multiple blood pressure signals are used to training the machine learning model, the first model may indicate a relationship between the blood pressure and the PPG signal. As another example, when a machine learning model is trained based on multiple PPG signals, the first model may be generated by training the trained machine learning model based on multiple blood pressure signals corresponding to the multiple PPG signals. As used herein, the corresponding blood pressure signal and PPG signal may refer to that the a blood pressure signal and the PPG signal may correspond to the same subject and generated by the subject simultaneously. In some embodiments, the blood pressure signal may be estimated by the PPG signal and/or an EEG signal. Then the first model may be generated by training the machine learning model based on the multiple PPG signals and/or EEG signals relating to multiple subjects and the blood pressure signals estimated based on the PPG signals and/or EEG signals.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 800 may further include preprocessing the multiple physiological data. As another example, operations 802 and 804 may be performed simultaneously. In some embodiments, process 800 may further include testing the first model. The first model may be tested based on multiple test data. The test data may include at least one portion of the multiple physiological features extracted in 804.

FIG. 9 is a flowchart illustrating an exemplary process 900 for identifying a subject based on a physiological signal according to some embodiments of the present disclosure. In some embodiments, one or more operations of process 900 illustrated in FIG. 9 may be implemented in the identification system 100 illustrated in FIG. 1. For example, the process 900 illustrated in FIG. 9 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3). In some embodiments, operation 708 may be performed according to process 900.

In 902, one or more physiological features may be extracted from physiological data relating to a subject to be identified. Operation 902 may be performed by the second feature extraction sub-unit. In some embodiments, the physiological data may include one or more physiological signals, personalized data, or other physiological data as described elsewhere in the disclosure. The physiological data may be obtained as described in connection with operation 602 as described in FIG. 6.

In 904, a first feature vector may be determined based on the physiological features relating to the subject to be identified. Operation 904 may be performed by the calculation sub-unit 546. In some embodiments, the first feature vector may include one or more dimensions. Each of the one or more dimensions may include a plurality of elements. The plurality of elements may include multiple values of physiological features determined based on the same physiological signal (e.g., a PPG signal, an ECG signal, etc.) or one or more same physiological features. In some embodiments, the first feature vector may be determined based on at least one portion of the physiological features relating to the subject to be identified. For example, the physiological features relating to the subject to be identified may be processed based on a first model relating to a first reference physiological features as described elsewhere in the disclosure. See for example, FIG. 7 and descriptions thereof. The first feature vector may be determined based on the at least one portion of the physiological features corresponding to the first reference physiological features. As another example, the physiological features relating to the subject to be identified may be processed based on a second model relating to a second reference physiological features. The second model may correspond to a registration subject. See for example, FIG. 7 and descriptions thereof. The first feature vector may be determined based on the at least one portion of the physiological features corresponding to the second reference physiological features.

In 906, a second feature vector may be determined based on identification information relating to a registration subject. Operation 906 may be performed by the calculation sub-unit 546. In some embodiment, the identification information relating to the registration subject may be obtained from the storage 130, the terminal 140, the storage module 440, and/or any other storage as described in connection with operation 606. In some embodiments, the identification information relating to the registration subject may include one or more identification physiological features relating to the registration subject. The one or more identification physiological features may be used to identify the registration subject. The identification physiological features relating to the registration subject may be determined as described in connection with FIG. 7. In some embodiments, the second feature vector may include one or more dimensions. Each of the one or more dimensions may include a plurality of elements. The plurality of elements may include multiple values of physiological features determined based on the same physiological signal (e.g., a PPG signal, an ECG signal, etc.) or one or more same physiological features relating to the registration subject. In some embodiments, the identification information relating to the registration subject may include a personalized model relating to the registration subject (e.g., a second model relating to the registration subject as described in FIG. 7). The personalized model relating to the registration subject may determine identification physiological features relating to the registration subject based on physiological signals relating to the registration subject.

In 908, a determination may be made to be as that whether a distance between the first feature vector and the second feature vector satisfies a condition. Operation 908 may be performed by the judgment sub-unit 544. If the distance between the first feature vector and the second feature vector satisfies the condition, process 900 may proceed to operation 910. If the distance between the first feature vector and the second feature vector does not satisfy the condition, process 900 may proceed to operation 906. As used herein, the distance between the first feature vector and the second feature vector may refer to a difference between the first feature vector and the second feature vector (i.e., the subject to be identified and the registration subject). In some embodiments, the distance may include a Euclidean distance, a Manhattan distance, a Minkowski distance, a Chebyshev distance, a normalized Euclidean distance, etc. For example, the Euclidean distance between the first feature vector and the second feature vector may be determined based on a mean value of each of dimensions of the first feature vector and the second feature vector. In some embodiments, the condition may include a threshold. If the distance between the first feature vector and the second feature vector is less than the threshold, the condition may be satisfied. If the distance between the first feature vector and the second feature vector is equal to or exceeds the threshold, the condition may be not satisfied. In some embodiments, the threshold may be preset by a user via, for example, the terminal 140, or according to a system default.

In 910, a determination may be made to be as that the subject to be identified matches with the registration subject. Operation 910 may be performed by the judgment sub-unit 544. In some embodiments, if the distance between the first feature vector and the second feature vector is less than the threshold, the subject to be identified may be determined to match with the registration subject. In some embodiments, the identification of the subject to be identified may be obtained based on the registration subject. For example, personalized data relating to the registration subject may be obtained from, for example, the storage 130, the terminal 140, the storage module 440, the storage unit 560, and/or other storages.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, multiple second feature vectors corresponding to multiple second registration subjects may be determined simultaneously. The first feature vector may be compared with the multiple second feature vectors simultaneously. For example, distances between the first feature vector and multiple second feature vectors corresponding to multiple registration subjects may be determined. The first subject may match with one of the multiple second registration subjects corresponding to a minimum distance and/or the minimum distance may be less than the threshold.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor, at least one computer-readable storage medium, and a communication port connected to a measuring device, the method comprising:
   acquiring first physiological data relating to a first subject;
   extracting at least one first physiological feature from the first physiological data relating to the first subject;
   determining a first model relating to at least one first reference physiological feature;
   generating, based on the first model and the at least one first physiological feature, a second model, the second model relating to at least one second reference physiological feature corresponding to the second model;
   determining, based on the second model and the at least one first physiological feature, at least one identification physiological feature relating to the first subject, wherein the at least one identification physiological feature corresponds to the at least one second reference physiological feature;
   identifying a second subject based on the at least one identification physiological feature relating to the first subject;
   wherein the identifying a second subject based on the at least one first physiological feature relating to the first subject comprises:
      acquiring the at least one identification physiological feature relating to the first subject;
      determining at least one second physiological feature relating to the second subject;
      comparing the at least one second physiological feature relating to the second subject and the at least one identification physiological feature relating to the first subject; and
      identifying the second subject based on the comparison; and
   wherein the comparing the at least one second physiological feature relating to the second subject and the at least one identification physiological feature relating to the first subject comprises:
      determining a first feature vector based on the at least one identification physiological feature relating to the first subject;
      determining a second feature vector based on the at least one second physiological feature relating to the second subject;
      determining a distance between the first feature vector relating to the first subject and the second feature vector relating to the second subject; and
      comparing the distance between the first feature vector relating to the first subject and the second feature vector relating to the second subject with a threshold.

2. The method of claim 1, wherein the first physiological data relating to the first subject includes at least one of an electrocardiogram (ECG) signal or a photoplethysmogram (PPG) signal.

3. The method of claim 1, wherein the determining a first model relating to at least one first reference physiological feature comprises:
   acquiring multiple physiological data relating to multiple subjects;
   extracting physiological features relating to the multiple subjects from the multiple physiological data; and
   generating the first model by training a machine learning model based on the physiological features relating to the multiple subjects.

4. The method of claim 1, wherein the machine learning model is constructed based on at least one of a convolutional neural network, a long short-term memory network, a deep belief network, a generative adversarial network, a support vector machine, or a random forest model.

5. The method of claim 1, wherein the determining, based on the first model and the at least one first physiological feature, a second model comprises:
   determining at least one effective physiological feature based on the first model and the at least one first physiological feature, the at least one effective physiological feature corresponding to the at least one first reference physiological feature; and
   generating the second model corresponding to the first subject by training the first model by the at least one effective physiological feature.

6. The method of claim 1, wherein the determining, based on the first model and the at least one first physiological feature, a second model comprises:
   acquiring second physiological data relating to the first subject, the second physiological data corresponding to the first physiological data;
   generating a third model based on the first model and the at least one first physiological feature, the second model relating to at least one third reference physiological feature corresponding to the third model; and
   generating the second model by training the third model based on the second physiological data.

7. The method of claim 6, wherein
the second physiological data relating to the first subject includes at least one of blood pressure data, blood glucose data, heart rate data, or respiration rate data; and
the at least one first physiological feature includes at least one of an electrocardiogram (ECG) signal or a photoplethysmogram (PPG) signal.

8. The method of claim 1, wherein the determining at least one second physiological feature relating to the second subject includes:
acquiring at least one of the first model or the second model; and
determining the at least one second physiological feature relating to the second subject based on the at least one of the first model or the second model.

9. The method of claim 1, further comprising:
determining, in response to the determination that the distance is lower than or equal to the threshold, that the second subject matches with the first subject.

* * * * *